United States Patent [19]

Bimman

[11] Patent Number: 5,645,600
[45] Date of Patent: Jul. 8, 1997

[54] HIGH PERFORMANCE STEM FOR ARTHROPLASTY

[76] Inventor: Lev A. Bimman, 2747 Del Medio Ct. Apt. 301, Mountain View, Calif. 94040

[21] Appl. No.: 304,576

[22] Filed: Sep. 12, 1994

[51] Int. Cl.$^6$ .................................. A61F 2/30; A61F 2/32
[52] U.S. Cl. ................................................ 623/18; 623/23
[58] Field of Search .................. 623/23, 22, 20, 623/18, 16

[56] References Cited

U.S. PATENT DOCUMENTS

| | | | |
|---|---|---|---|
| 3,893,196 | 7/1975 | Hochman | 623/23 |
| 4,283,799 | 8/1981 | Pratt, Jr. et al. | 623/23 |
| 4,904,264 | 2/1990 | Scheunemann . | |
| 4,908,032 | 3/1990 | Keller | 623/23 |
| 4,908,034 | 3/1990 | Weightman et al. | 623/23 |
| 4,919,678 | 4/1990 | Kranz . | |
| 4,944,762 | 7/1990 | Link et al. . | |
| 4,950,300 | 8/1990 | Langlais . | |
| 4,963,155 | 10/1990 | Lazzeri et al. . | |
| 4,990,161 | 2/1991 | Kampner . | |
| 5,002,578 | 3/1991 | Luman . | |
| 5,041,140 | 8/1991 | Teinturier . | |
| 5,080,676 | 1/1992 | May | 623/23 |
| 5,080,679 | 1/1992 | Pratt et al. | 623/23 |
| 5,080,685 | 1/1992 | Bolesky et al. . | |
| 5,108,449 | 4/1992 | Gray . | |
| 5,108,452 | 4/1992 | Fallin . | |
| 5,116,379 | 5/1992 | McLardy-Smith . | |
| 5,135,529 | 8/1992 | Paxson et al. . | |
| 5,181,928 | 1/1993 | Bolesky et al. . | |
| 5,201,771 | 4/1993 | Belykh et al. . | |
| 5,201,882 | 4/1993 | Paxson . | |
| 5,286,260 | 2/1994 | Bolesky et al. . | |
| 5,316,550 | 5/1994 | Forte . | |

FOREIGN PATENT DOCUMENTS

| | | | |
|---|---|---|---|
| 2580171 | 10/1986 | France | 623/23 |
| 2700947 | 8/1994 | France | 623/23 |
| 2318396 | 10/1974 | Germany | 623/23 |
| 2724040 | 11/1978 | Germany | 623/23 |
| 2838335 | 3/1980 | Germany | 623/2 |
| 5137739 | 6/1993 | Japan | 623/23 |

OTHER PUBLICATIONS

J. Dennis Bobyn; "Flexibility Must Increase in Femoral Stem"; Orthopedic Special Edition, vol. 2 No. 10, 1993; pp. 14 and 20.

*Primary Examiner*—David Isabella
*Attorney, Agent, or Firm*—Michaelson & Wallace

[57] ABSTRACT

A two-part prosthesis, including a stem and head portion, for a hip or other joint is provided. Briefly stated, a intramedullary stem is provided having flexibility that is comparable to that of the surrounding bone. The intramedullary stem comprises a strong and resilient core that is coated with a biocompatible material. The flexibility of the stem distributes the loading forces from the joint more uniformly over the supporting bone with the result that bone degeneration from stress shielding is minimized or eliminated. Additionally, the prosthesis head is made of entirely biocompatible materials and is shaped so as to fit conventional joint sockets. The modular, two-part structure of the prosthesis allows the stem and head portions to be selected to provide the best fit for the patient.

12 Claims, 2 Drawing Sheets

HIGH PERFORMANCE STEM FOR ARTHROPLASTY

BACKGROUND

1. Technical Field

This invention relates to a prosthesis for use in joint replacement. More particularly, the present invention relates to a modular prosthesis for replacement of the head portion of the femur, which may be adapted to other joints such as the elongated bone of the shoulder.

2. Background Art

There are various diseases and injuries affecting joints that cause restriction of the joint, loss of movement and pain. Arthroplasty is the surgical treatment of these disorders and aims at restoration of movement at the joint.

Previously, prosthesis components, and particularly femoral prosthesis components that are utilized for surgical reconstruction of a human hip joint, have incorporated relatively stiff intramedullary fixation stems. These stems are fabricated of suitable, biocompatible metallic alloys and generally have integral neck and head portions. Because the stems of these components are stiff, they do not provide significant flexure along their length. However, the surrounding bone within which the stem is implanted is somewhat flexible. Therefore, a stiff stem, relative to the more flexible structure of the bone, results in a composite structure wherein the flexural rigidity of the constituent parts varies significantly.

The use of relatively stiff intramedullary stems has been clinically suspected of producing adverse and destructive bone reactions over a long period of time. Conventional relatively stiff stems reduce the forces distributed to surrounding bone to levels significantly below normal anatomical levels of an intact femur. More particularly, stiff stems can also be attributed to the development of reduced levels of force or stress shielding within the surrounding support of bone structure. In addition, stiff stems can be attributed to producing micromotion at the stem and bone interface. Both the presence of interface micromotion and the reduced stresses on the bone can result in adverse bone reactions which have been attributed to the diminution of bone mass at the interface and also within the surrounding bone matrix. Understandably, loss of bone is detrimental to the function of the implant and can produce loosening of the prosthesis and accompanying loss of articular joint or hip function. Therefore, under the influence of reduced levels of bone stress distribution incident to stiff conventional stems, adverse bone reaction may occur postoperatively where the adjacent bone structure degenerates, diminishes or atrophies. This resultant bone loss can seriously affect the structural integrity of the adjacent supportive bone and may ultimately lead to significant loss or compromise of the long-term function of the implant prosthesis if the resulting pain and/or loss of function becomes significantly intolerable to the patient. Depending upon the severity of these functional factors, surgical revision may be indicated.

Since femoral stem stiffness is the major cause of bone resorption or atrophy, a more flexible stem would be desirable. However, a more flexible femoral stem would have to provide adequate strength to endure the stresses of the body. A variety of ways have been identified to increase stem flexibility.

Geometric changes have been employed to reduce femoral stem stiffness, such as flutes, slots or hollowed cores. A problem with flutes, slots and hollow cores is that while they impart increased flexibility, they decrease the strength of the prosthesis because they require cutting away of some of the supporting structure of the stem.

In addition to researching new geometries to reduce femoral stiffness, there has been research into developing some composite material that would provide both flexibility and strength. However, these efforts have not been very successful. Much work has been done in the area of using biocompatible alloys. However, these biocompatible alloys have insufficient shearing strength, insufficient resistance to impact and an insufficient endurance limit. The possibility of improving the strength of these biocompatible alloys appears limited. Biocompatible metals with relatively increased flexibility, such as titanium have been used. However, these materials have proved brittle and not strong enough to withstand the stresses of the body. An additional problem with titanium is that it has a notch sensitivity such that it requires careful engineering and design in particular when a porous coating to allow bone ingrowth is applied. The notch sensitivity is an indication of the extent to which the endurance of metals, as determined on smooth and polished specimens, is reduced by surface discontinuities such as tool marks, notches and changes in section. Notch sensitivity increases with hardness and endurance limit. Therefore, titanium is more susceptible to failure if its surface is not smooth.

Conventional prostheses for the replacement of the head portion of the femur are also generally unitary structures. The conventional prosthesis generally includes a stem portion that is designed to extend into the intramedullary cavity within the femur. The stem portion may be secured within the femur by the use of bone cement or other adaptations. The conventional hip prosthesis includes a stem and an integral head portion as mentioned above. The head portion is designed to fit into a joint socket. Since the prosthesis is all one piece the unit is normally entirely of the same materials. This has limited the types of materials used since the prostheses has to be both biocompatible and strong.

In addition, because conventional prostheses are generally unitary devices, the practice has been to maintain a large inventory of differently sized units to accommodate the different sizes of bones. Generally, the patient is evaluated by x-ray or some other means to determine the approximate bone size. Then a prosthesis range is estimated. During the replacement operation, several prostheses within the estimated range are made available, as suggested by the evaluation. The appropriate prosthesis is then selected for insertion into the patient at the time of operation.

Therefore, what is needed is a prosthesis which provides reduced femoral stem stiffness, strength sufficient to withstand the stresses of the weight of the body to avoid failure or permanent deformation, biocompatibility and a good fit to the patient.

SUMMARY

Wherefore, it is the object of the present invention is to provide a prosthesis for joint replacement that provides an intramedullary stem portion that is made of high-strength materials, but that is resilient and flexible, so that the stem springs back to its original shape after a stress has been removed, so that the stem more closely resembles the bending characteristics of the surrounding bone.

Wherefore, it is another object of this invention to provide a prosthesis for joint replacement, where the intramedullary stem is constructed of strong, resilient material, and is insulated with a material that is body-compatible so as to provide a completely biocompatible surface of the prosthesis.

Wherefore, it is another object of the present invention to provide a prosthesis for joint replacement, where the intramedullary stem portion of the prosthesis is insulated from the head portion which is constructed of body-compatible material, thus preventing an electrochemical interaction between the two portions of the prosthesis.

Wherefore, it is another object of the present invention to provide a prosthesis for joint replacement that consists of a multi-part construction such that the head and intramedullary stem portions of the prosthesis may be made of different materials.

Wherefore, it is still another object of this invention to provide a prosthesis for joint replacement whereby rotation between the stem and head parts of the prosthesis is prevented.

Wherefore, still another object of this invention is to provide a prosthesis for joint replacement that is modular and that has a great deal of flexibility in its assembly as to the size of the assembled device.

Wherefore, still another object of the present invention is to provide a prosthesis for joint replacement that may be assembled in the operating room before any component is inserted into the patient.

The foregoing objects have been attained by the present invention that is directed to a joint prosthesis that provides a strong, resilient stem portion, and also having the advantages of a modular design. This joint prosthesis includes: (1) a stem portion for insertion into the intramedullary canal of the elongated bone of which the stem core is made of a strong, resilient material which is not necessarily body compatible and which has flexure characteristics substantially similar to that of the elongated bone. A body-compatible coating completely covers the exterior surface of the stem core, thus insulating the stem core from surrounding body fluids and tissues; (2) a head portion made of a body-compatible material for interfacing with a conventional joint socket; and (3) a connector for connecting the stem and head portions. This joint prosthesis also provides an insulation layer between the stem core and the head portion thereby preventing a reaction between the two parts if they are made of electrochemically incompatible materials. The head and stem portions of the joint prosthesis may be connected by a threaded screw. The head of the prosthesis is shaped so as to be compatible with existing joint sockets and includes a stepped through-hole for receiving the screw. The stem of the prosthesis also includes a hole to receive the screw. The screw head is insulated from the fluids and tissues of the body by a body-compatible material placed in a hole in the head of the prosthesis so that it completely encases the screw head therein. An insulating insert, that has a hollow cylindrical extension slightly larger than the screw shank and which is placed into the bottom of the stepped through-hole may also be installed prior to the insulating compound. If this alternative is employed then the screw head will rest on the annular top of the insert. Additionally, an anti-rotation means to prevent rotation between the head and stem portions is provided. This includes a cylindrical extension, which is flat on two parallel sides, projecting from the end of the stem portion which mates with the head portion. The head portion has a hole corresponding in shape to the cylindrical extension of the stem portion. Whenever the stem portion is connected to the head portion, the flat surfaces of the cylindrical extension mate with corresponding flat surfaces of the receiving hole thereby preventing rotation between the stem portion and the head portion. Alternately, an anti-rotation device which consists of a layer of adhesive between the head and stem portions of the prosthesis may be employed. An alternate joint prosthesis embodiment incorporates a connector which comprises a threaded pin projecting from an end of the head portion which mates with a threaded hole in the stem portion. The joint prostheses stem and head portions can be made in a variety of sizes such that the stem portion has a size corresponding to the intramedullary canal of the patient and the head portion has a size corresponding to a joint socket suitably sized for the patient.

Advantages provided by the aforementioned joint prosthesis include an increased intramedullary stem strength and resiliency to avoid breakage or deformation of the prosthesis under the weight and typical stresses of the body. The increased flexibility of the intramedullary stem, resembling that of the surrounding bone, reduces or eliminates the abnormal and reduced bone stresses that can result in adverse bone reactions which have been attributed to loss of bone mass, loosening of the prosthesis, loss of joint function, and that may result in severe pain. The stronger, more resilient stem portion, allowing the stem to spring back to its original shape after a stress has been removed, is especially advantageous in hip replacements, since the stem portion placed in the femur is subject to much stress due to the weight of the body. Since all exposed surfaces of the prosthesis are sealed by, or constructed of, body-compatible materials, the prosthesis is completely biocompatible despite having the characteristics of a strong, flexible intramedullary stem. Additionally, the head and intramedullary stem portions of the invention, as they are joined in the manner provided for in this prosthesis, are insulated so as to prevent contact between the parts, thus avoiding any electrochemical reaction due dissimilar metals being used. The stem and head are joined so as to prevent any detrimental rotation. In addition, the two-part structure has the advantage of providing improved strength and flexibility to the stem portion that was previously susceptible to failure, while retaining the biocompatible head portion that interfaces with a conventional hip and shoulder socket prosthesis. The two-part structure also allows suitably sized stem and head portions to be matched, thus resulting in a better fit to the patient than a unitary prosthesis, while not requiring as large of an inventory to be kept on hand to facilitate such an improved match.

Accordingly, it can be seen that all the stated objectives of the invention have been accomplished by the above-described embodiments of the present invention. In addition, other objectives, advantages and benefits of the present invention will become apparent from the detailed description that follows hereinafter when taken in conjunction with the drawing figures which accompany it.

DESCRIPTION OF THE DRAWINGS

These and other features, aspects, and advantages of the present invention will become better understood with regard to the following description, appended claims, and accompanying drawings where:

DETAILED DESCRIPTION OF THE PREFERRED EMBODIMENTS

Figures 1A, 1B:
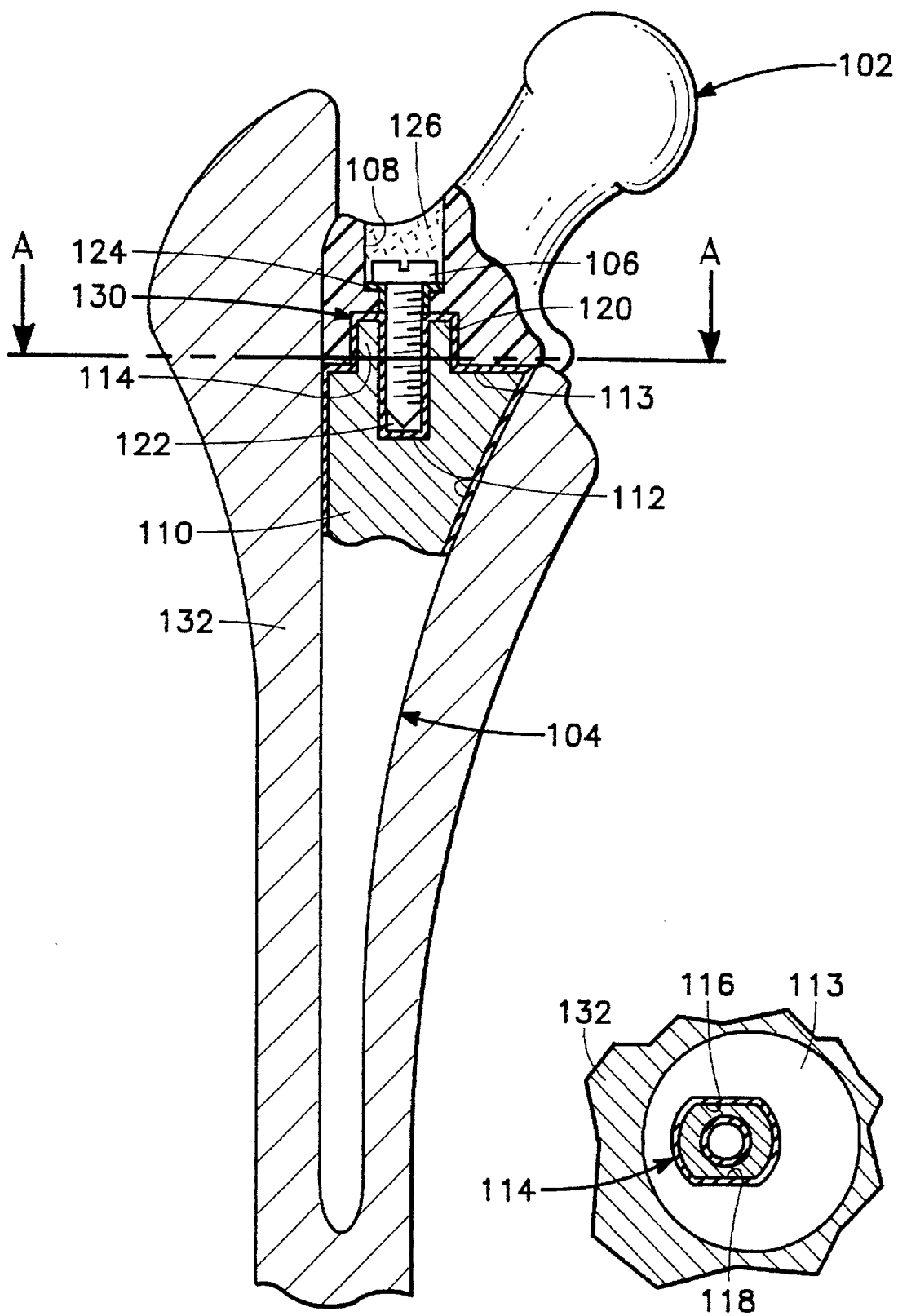
FIG. 1A is a partially cut away view of a joint prosthesis in accordance with the present invention shown installed in a bone.
FIG. 1B provides a cross-sectional view of the joint prosthesis of FIG. 1A taken at A—A.

Preferred embodiments of the present invention will now be described with reference to the drawings. A preferred version of the invention as used in a hip replacement is provided in FIGS. 1A and 1B. In this form, the invention includes a head part 102 to be received into a conventional hip socket (not shown), an intramedullary stem part 104 and a connector 106, which is preferably a screw, that connects the head and intramedullary stem portions of the prosthesis together. The intramedullary stem 104 is comprised of a stem core 110, which is covered with a film of body-compatible insulating compound 112. The top surface 113 of the intramedullary stem 104 of the prosthesis is flat and has a raised cylindrical section 114 with opposing flat surfaces 116 and 118. The raised cylindrical section 114 has a flat top 120 with a centrally located hole 122 to receive the connector 106. This hole 122 is also coated with body-compatible insulating compound 112, and is threaded to receive the connector 106. The cylindrical section 114, is somewhat offset on the top surface of the intramedullary surface 113 to match a correspondingly shaped hole 130 in the head portion 102. The lower surface of the head 102 has a hole 130 which is designed to receive the raised cylindrical portion 114 of the stem part 104 of the prosthesis. The flats 116, 118 of the cylindrical section 114, when mated with flats in the hole 130 in the head 102, prevent rotation between the stem 104 and the head 102. However, other anti-rotational devices may be used as, for instance the two pieces could simply be glued together. The threaded hole 122 extends to a depth sufficient to receive the screw 106. The stem core 110, of the intramedullary stem 104, is made of strong, resilient material such that it returns to its original shape when stresses are removed and does not break or permanently deform under the normal stresses of the body. Additionally, the material is flexible enough to resemble the characteristics of the surrounding bone. The head 102 is shaped so to be compatible with existing joint sockets. The head 102 of the prosthesis includes a stepped through-hole 108 for receiving the screw 106. This stepped through-hole 108 in the head portion 102 has an upper section having a diameter slightly larger than a diameter of a head of the screw and an annular bottom corresponding in shape to the underside of the screw head. The lower section of the hole 108 has a diameter slightly greater than the diameter of a shank of the screw 106. The head of the screw 106 rests on the annular bottom of the upper section of the stepped hole 108 once the screw 106 is installed in the stem 104. However, an insulating insert 124 may be placed in hole 108 prior to receiving the screw 106 to insulate the screw from the head if the two are made of incompatible materials that might react electrochemically. The insulating insert 124 has a hollow cylindrical extension which extends into the lower section of the stepped through-hole 108 of the head portion 102. This insert 124 may be made of the same biocompatible compound as insulating compound 112. After the stem 104 and head 102 portions of the prosthesis have been connected by the screw 106 the hole 108 is filled with a self-hardening biocompatible insulating material 126, which might be made of the same biocompatible material as the insulating compound 112.

This prosthesis, once assembled, may be inserted in a hole of femur 132 with cement or other methods of fixation well known in the art.

Figure 2:
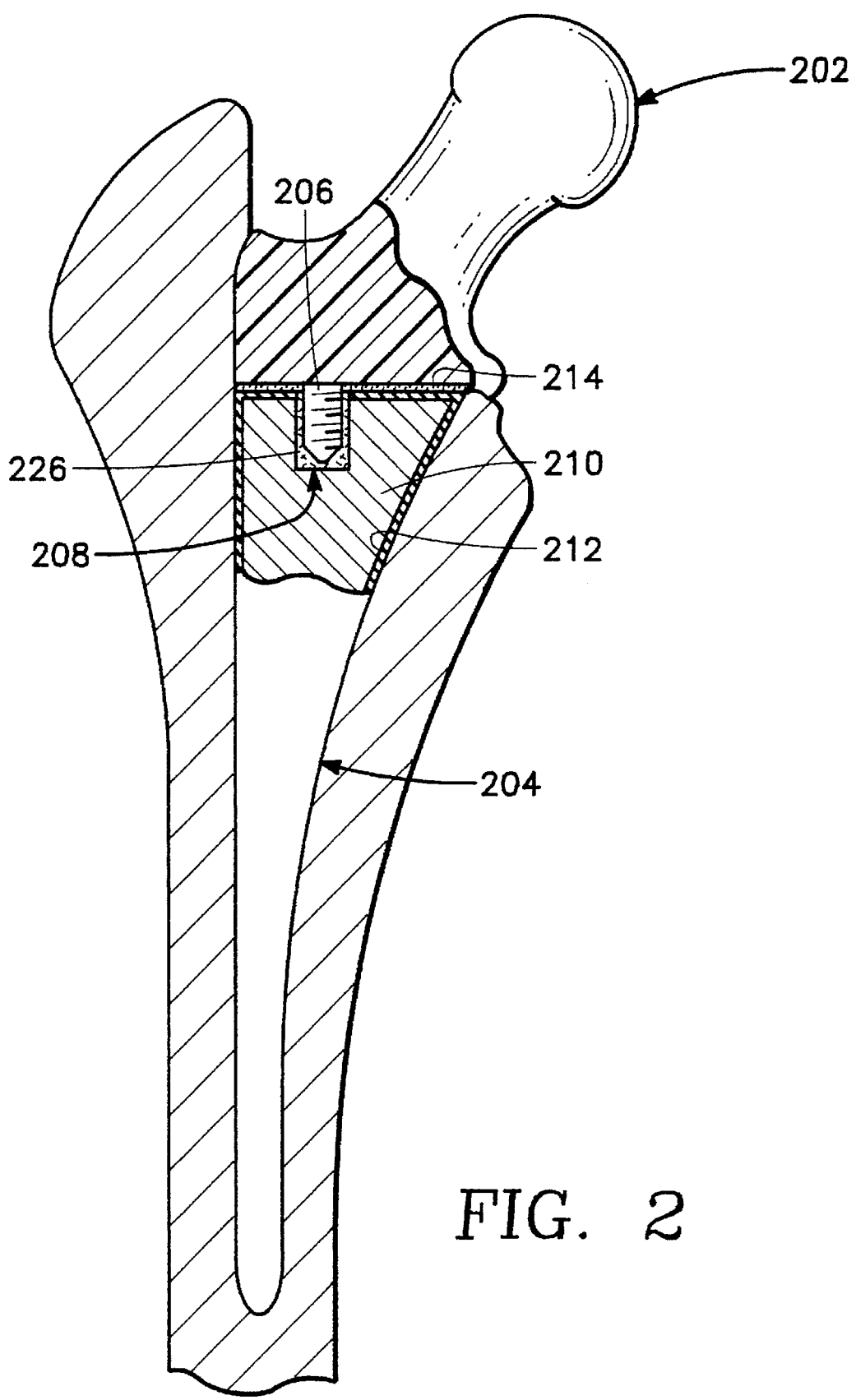
FIG. 2 is a partially cut away view of a joint prosthesis in accordance with an alternate embodiment of the present invention shown installed in a bone.

Another preferred embodiment of the present invention is illustrated in FIG. 2. This embodiment of the joint prosthesis generally includes all the elements of the joint prosthesis of FIGS. 1A and 1 B, with the following exceptions. The head portion 202 has a threaded pin 206, corresponding to the threads of insulating compound 226 inserted in hole 208 of the stem 204. There is no hole in the head portion 202, and hence no insulating insert or insulating compound 226 is required in the head 202. This embodiment does not employ an anti-rotation cylinder on the stem 210 to be mated with a corresponding hole in the head 202 section. Rather, the head 202 is screwed onto the stem 210, and the head and stem parts of the invention are secured by a layer of adhesive 214 to prevent rotation.

The insulating compounds 226, 212, 112, 126 are materials that are compatible with the body of a patient and appropriate for permanent contact with the bone and surrounding tissues. The compound coating the stem 104, 204 is also sufficiently flexible so as to prevent cracking when the stem 104, 204 flexes. An example of an appropriate compound is an acrylic dental cement, such as that sold under the mark "Simplex Rapid". However, this is not meant to limit the present invention in regard to the insulating compound by virtue of the disclosure of a specific example thereof. The compound can be any material with the aforementioned qualities. The intramedullary stem 110, 210 is preferably made of a resilient, hardened steel, for example spring steel, or other materials providing the aforementioned resiliency and strength and with similar flexibility to the bone. The adhesive 214, may be any standard biocompatible resin-based adhesive strong enough in shear to prevent rotation between the head and stem portions once dried. The head portion 102, 202 is made entirely of body-compatible material as known in the prior art and shaped to fit a conventional hip socket.

Since the intramedullary stem stiffness of the prosthesis will allow the stem 104, 204 to have flexibility which is comparable to that of the surrounding bone, this flexibility will distribute the loading forces from the joint more uniformly over the supporting bone with the result that bone degeneration from stress shielding is minimized or eliminated. The resiliency of the stem portion 104, 204 will allow them to spring back to their original shape after a stress has been removed.

The increased strength of the stem 104, 204 will help to avoid breakage or deformation of the prostheses under the weight and typical stresses of the body. Since the coating 112, 212 on the stem 104, 204 provides a body-compatible seal, it is not necessary to use brittle body-compatible materials for the construction of the stem 104, 204. This feature of the invention overcomes the problems with the use of biocompatible metals which are quite brittle and lack the strength and resiliency of, for example, spring steel, causing them to fail or deform under stress. Additionally, the increased flexibility of the intramedullary stem 104, 204 resembling that of the surrounding bone, reduces or eliminates the abnormal and reduced bone stresses that can result in adverse bone reactions which have been attributed to loss of bone mass, loosening of the prosthesis, loss of joint function, and that may result in severe pain.

The two-part structure of the prosthesis allows improved strength and flexibility to the stem 104, 204 that was previously susceptible to failure, while retaining the biocompatible head 102, 202 portions that interfaces with a conventional hip and shoulder socket prosthesis. The insulating material 112, 212 which coats the stem 104, 204 and insulates the head 102, 202 from the stem 104, 204 avoids material mismatches which may result in problems such as electrochemical reaction. The insulating compound 126, 226 used to insulate the connector 106, 206 and the insulating insert 124 also serve this purpose.

Additionally, the two-part structure of the prosthesis allows a sizing of the head part 102, 202 and stem part 104, 204 of the prosthesis to provide for a better fit to the patient than a unitary prosthesis would provide. The two-part structure also allows hospitals to maintain a lesser inventory of prostheses on hand and still fit the patient with a suitable prosthesis since a greater combination of prostheses sizes can be created with the two-part structure than would be available with the same number of parts for a unitary prosthesis. Also, the present invention provides a modular hip prosthesis that may be assembled in the operating room before any component is inserted into the patient.

While the invention has been described in detail by reference to the preferred embodiments described above, it is understood that variations and modifications thereof may be made without departing from the true spirit and scope of the invention. For example, similar prostheses may be adapted to fit other joints. Additionally, modification of the embodiments may allow for adaptation for use in animals.

Wherefore what is claimed is:

1. A joint prosthesis for replacement of the articular head of an elongated bone, comprising:
   (a) a stem portion for insertion into the intramedullary canal of the elongated bone comprising,
      (a1) a stem core made of a strong resilient material which is not body-compatible and which has flexure characteristics substantially similar to that of the elongated bone, said stem core consisting of one of (i) spring steel, or (ii) hardened steel,
      (a2) an insulation layer completely covering the exterior surface of the stem core, said insulation layer being made of a body compatible material and insulating the stem core from surrounding body fluids and tissues;
   (b) a head portion made of a body-compatible material for interfacing with a joint socket of an adjacent bone; and,
   (c) a means for connecting the stem and head portions.

2. The joint prosthesis in accordance with claim 1, wherein:
   (a) the material making up the stem core and head portion are incompatible in that the materials react electrochemically; and,
   (b) the insulation layer further insulates the stem core from the head portion thereby preventing an electrochemical reaction therebetween.

3. The joint prosthesis in accordance with claim 1, wherein the connecting means comprises:
   (a) a screw;
   (b) a threaded hole in the stem portion having threads corresponding to threads of the screw;
   (c) a stepped through-hole in the head portion comprising,
      (c1) an upper section having a diameter slightly larger than a diameter of a head of the screw and annular bottom corresponding in shape to an underside of the screw head, and,
      (c2) a lower section having a diameter slightly greater than a diameter of a shank of the screw;
   (d) a means for insulating the screw head from the fluids and tissues of the body; and wherein,
   (e) the screw is threadable into the threaded hole of the stem portion through the stepped through-hole of the head portion such that the underside of the screw head rests on annular bottom of the upper section of the stepped hole.

4. The joint prosthesis in accordance with claim 3, wherein the insulating means comprises:
   a body-compatible material disposed in the upper section of the stepped hole such that the upper section is filled and the screw head is completely covered.

5. The joint prosthesis in accordance with claim 3, wherein the material making up the head portion is incompatible with a material making up the screw in that the materials react electrochemically, and further comprising:
   a second means for insulating the screw from the head portion, thereby preventing an electrochemical reaction therebetween.

6. The joint prosthesis in accordance with claim 5, wherein the annular bottom of the upper section of the stepped through-hole of the head portion is flat, and wherein the second insulating means comprises:
   an insulating insert disposed between the annular bottom of the upper section and the underside of the screw head.

7. The joint prosthesis in accordance with claim 1, further comprising:
   an anti-rotation means for preventing relative rotation between the stem portion and the head portion.

8. The joint prosthesis in accordance with claim 7, wherein the anti-rotation means comprises:
   (a) a cylindrical extension projecting from an end of the stem portion which interfaces with the head portion, said cylindrical portion having two opposing longitudinally disposed flat surfaces; and,
   (b) a receiving hole in the head portion corresponding in shape to the cylindrical extension of the stem portion; wherein,
   (c) whenever the stem portion is connected to the head portion, the flat surfaces of the cylindrical extension mate with corresponding flat surfaces of the receiving hole thereby preventing rotation between the stem portion and the head portion.

9. The joint prosthesis in accordance with claim 1, wherein the connecting means comprises:
   (a) a threaded pin projecting from an end of the head portion connectable to the stem portion; and,
   (b) a threaded hole in the stem portion having threads corresponding to threads of the threaded pin; and wherein,
   (c) the threaded pin is threadable into the threaded hole of the stem portion, thereby connecting the stem portion and the head portion.

10. The joint prosthesis in accordance with claim 9, further comprising:
    an anti-rotation means for preventing relative rotation between the stem portion and the head portion.

11. The joint prosthesis in accordance with claim 10 wherein the anti-rotation means comprises:
    a layer of adhesive disposed between the stem portion and the head portion.

12. A joint prosthesis kit for replacement of the articular head of an elongated bone, comprising:
    (a) a stem portion taken from a group of stems having a distribution of sizes, for insertion into the intramedullary canal of the elongated bone comprising, (a1) a stem core made of a strong resilient material which is not body-compatible and which has flexure characteristics substantially similar to that of the elongated bone, said stem core consisting of one of (i) spring steel, or (ii) hardened steel, (a2) an insulation layer completely covering the exterior surface of the stem core, said insulation layer being made of a body compatible material and insulating the stem core from surrounding body fluids and tissues;

(b) a head portion taken from a group of heads having a distribution of sizes, made of a body-compatible material for interfacing with a joint socket of an adjacent bone; and (c) a means for connecting the stem and head portions;

(d) the stem portion chosen to have a size corresponding to the intramedullary canal of the elongated bone into which the stem portion is to be inserted and the head portion chosen to have a size corresponding to the joint socket with which the head portion is to be interfaced.

* * * * *